United States Patent
Chen

(10) Patent No.: US 10,561,519 B2
(45) Date of Patent: Feb. 18, 2020

(54) WEARABLE COMPUTING DEVICE HAVING A CURVED BACK TO REDUCE PRESSURE ON VERTEBRAE

(71) Applicant: Toyota Motor Engineering & Manufacturing North America, Inc., Erlanger, KY (US)

(72) Inventor: Tiffany Chen, San Jose, CA (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 196 days.

(21) Appl. No.: 15/215,379

(22) Filed: Jul. 20, 2016

(65) Prior Publication Data

US 2018/0021161 A1 Jan. 25, 2018

(51) Int. Cl.

| | |
|---|---|
| *G06F 1/16* | (2006.01) |
| *G06F 3/01* | (2006.01) |
| *G06K 9/00* | (2006.01) |
| *H04N 5/232* | (2006.01) |
| *G09B 21/00* | (2006.01) |
| *A61F 5/02* | (2006.01) |
| *A45F 5/00* | (2006.01) |

(52) U.S. Cl.
CPC .............. *A61F 5/026* (2013.01); *A45F 5/00* (2013.01); *G06F 1/163* (2013.01); *A45F 2005/006* (2013.01); *A45F 2200/0525* (2013.01)

(58) Field of Classification Search
CPC ........ A61F 5/026; G06F 1/1686; G06F 1/163; A45F 5/00; A45F 2200/0525; A45F 2005/006

USPC ........................................................ 348/62
See application file for complete search history.

(56) References Cited

U.S. PATENT DOCUMENTS

| 4,520,501 A | 5/1985 | DuBrucq |
| 4,586,827 A | 5/1986 | Hirsch et al. |
| | (Continued) | |

FOREIGN PATENT DOCUMENTS

| CN | 201260746 | 6/2009 |
| CN | 101527093 | 9/2009 |
| | (Continued) | |

OTHER PUBLICATIONS

Zhang, Shanjun; Yoshino, Kazuyoshi; A Braille Recognition System by the Mobile Phone with Embedded Camera; 2007; IEEE.

(Continued)

*Primary Examiner* — Susan E. Hodges
(74) *Attorney, Agent, or Firm* — Snell & Wilmer LLP

(57) ABSTRACT

A wearable computing device includes a first side portion and a second side portion that partially extend across a shoulder and rest on a front of a user. The device also includes a neck portion connected to the first side portion and the second side portion. The neck portion includes an outer edge and an inner edge. The neck portion is curved from the first side portion to the second side portion to extend around a portion of a circumference of the neck of the user. The neck portion is also curved from the outer edge to the inner edge to follow a curvature of a spine of the user. The wearable computing device also includes an input device and a mobile processor designed to determine output data based on input data. The wearable computing device also includes an output device designed to output the output data.

16 Claims, 6 Drawing Sheets

(56) References Cited

U.S. PATENT DOCUMENTS

| | | |
|---|---|---|
| 4,786,966 A | 11/1988 | Hanson |
| 5,047,952 A | 9/1991 | Kramer |
| 5,097,856 A | 3/1992 | Chi-Sheng |
| 5,129,716 A | 7/1992 | Holakovszky et al. |
| 5,233,520 A | 8/1993 | Kretsch et al. |
| 5,265,272 A | 11/1993 | Kurcbart |
| 5,463,428 A | 10/1995 | Lipton et al. |
| 5,508,699 A | 4/1996 | Silverman |
| 5,539,665 A | 7/1996 | Lamming et al. |
| 5,543,802 A | 8/1996 | Villevieille et al. |
| 5,544,050 A | 8/1996 | Abe |
| 5,568,127 A | 10/1996 | Bang |
| 5,636,038 A | 6/1997 | Lynt |
| 5,659,764 A | 8/1997 | Sakiyama |
| 5,701,356 A | 12/1997 | Stanford et al. |
| 5,733,127 A | 3/1998 | Mecum |
| 5,780,756 A * | 7/1998 | Babb .................... G10D 3/18 84/280 |
| 5,807,111 A | 9/1998 | Schrader |
| 5,872,744 A | 2/1999 | Taylor |
| 5,953,693 A | 9/1999 | Sakiyama |
| 5,956,630 A | 9/1999 | Mackey |
| 5,982,286 A | 11/1999 | Vanmoor |
| 6,009,577 A | 1/2000 | Day |
| 6,055,048 A | 4/2000 | Langevin et al. |
| 6,067,112 A | 5/2000 | Wellner et al. |
| 6,199,010 B1 | 3/2001 | Richton |
| 6,229,901 B1 | 5/2001 | Mickelson et al. |
| 6,230,135 B1 | 5/2001 | Ramsay |
| 6,230,349 B1 | 5/2001 | Silver et al. |
| 6,285,757 B1 | 9/2001 | Carroll et al. |
| 6,307,526 B1 | 10/2001 | Mann |
| 6,323,807 B1 | 11/2001 | Golding et al. |
| 6,349,001 B1 | 2/2002 | Spitzer |
| 6,466,232 B1 | 10/2002 | Newell et al. |
| 6,477,239 B1 | 11/2002 | Ohki |
| 6,542,623 B1 | 4/2003 | Kahn |
| 6,580,999 B2 | 6/2003 | Maruyama et al. |
| 6,594,370 B1 | 7/2003 | Anderson |
| 6,603,863 B1 | 8/2003 | Nagayoshi |
| 6,619,836 B1 | 9/2003 | Silvant et al. |
| 6,701,296 B1 | 3/2004 | Kramer |
| 6,774,788 B1 | 8/2004 | Balfe |
| 6,825,875 B1 | 11/2004 | Strub et al. |
| 6,826,477 B2 | 11/2004 | Ladetto et al. |
| 6,834,373 B2 | 12/2004 | Dieberger |
| 6,839,667 B2 | 1/2005 | Reich |
| 6,857,775 B1 | 2/2005 | Wilson |
| 6,920,229 B2 | 7/2005 | Boesen |
| D513,997 S | 1/2006 | Wilson |
| 7,027,874 B1 | 4/2006 | Sawan et al. |
| D522,300 S | 6/2006 | Roberts |
| 7,069,215 B1 | 6/2006 | Bangalore |
| 7,106,220 B2 | 9/2006 | Gourgey et al. |
| 7,228,275 B1 | 6/2007 | Endo |
| 7,299,034 B2 | 11/2007 | Kates |
| 7,308,314 B2 | 12/2007 | Havey et al. |
| 7,336,226 B2 | 2/2008 | Jung et al. |
| 7,356,473 B2 | 4/2008 | Kates |
| 7,413,554 B2 | 8/2008 | Kobayashi et al. |
| 7,417,592 B1 | 8/2008 | Hsiao et al. |
| 7,428,429 B2 | 9/2008 | Gantz et al. |
| 7,463,188 B1 | 12/2008 | McBurney |
| 7,496,445 B2 | 2/2009 | Mohsini et al. |
| 7,501,958 B2 | 3/2009 | Saltzstein et al. |
| 7,525,568 B2 | 4/2009 | Raghunath |
| 7,564,469 B2 | 7/2009 | Cohen |
| 7,565,295 B1 | 7/2009 | Hernandez-Rebollar |
| 7,598,976 B2 | 10/2009 | Sofer et al. |
| 7,618,260 B2 | 11/2009 | Daniel et al. |
| D609,818 S * | 2/2010 | Tsang .................... D24/215 |
| 7,656,290 B2 | 2/2010 | Fein et al. |
| 7,659,915 B2 | 2/2010 | Kurzweil et al. |
| 7,743,996 B2 | 6/2010 | Maciver |
| D625,427 S * | 10/2010 | Lee .................... D24/214 |
| 7,843,351 B2 | 11/2010 | Bourne |
| 7,843,488 B2 | 11/2010 | Stapleton |
| 7,848,512 B2 | 12/2010 | Eldracher |
| 7,864,991 B2 | 1/2011 | Espenlaub et al. |
| 7,938,756 B2 | 5/2011 | Rodetsky et al. |
| 7,991,576 B2 | 8/2011 | Roumeliotis |
| 8,005,263 B2 | 8/2011 | Fujimura |
| 8,035,519 B2 | 10/2011 | Davis |
| D649,655 S | 11/2011 | Petersen |
| 8,123,660 B2 | 2/2012 | Kruse et al. |
| D656,480 S | 3/2012 | McManigal et al. |
| 8,138,907 B2 | 3/2012 | Barbeau et al. |
| 8,150,107 B2 | 4/2012 | Kurzweil et al. |
| 8,177,705 B2 | 5/2012 | Abolfathi |
| 8,239,032 B2 | 8/2012 | Dewhurst |
| 8,253,760 B2 | 8/2012 | Sako et al. |
| 8,300,862 B2 | 10/2012 | Newton et al. |
| 8,325,263 B2 | 12/2012 | Kato et al. |
| D674,501 S | 1/2013 | Petersen |
| 8,359,122 B2 | 1/2013 | Koselka et al. |
| 8,395,968 B2 | 3/2013 | Vartanian et al. |
| 8,401,785 B2 | 3/2013 | Cho et al. |
| 8,414,246 B2 | 4/2013 | Tobey |
| 8,418,705 B2 | 4/2013 | Ota et al. |
| 8,428,643 B2 | 4/2013 | Lin |
| 8,483,956 B2 | 7/2013 | Zhang |
| 8,494,507 B1 | 7/2013 | Tedesco et al. |
| 8,494,859 B2 | 7/2013 | Said |
| 8,538,687 B2 | 9/2013 | Plocher et al. |
| 8,538,688 B2 | 9/2013 | Prehofer |
| 8,571,860 B2 | 10/2013 | Strope |
| 8,583,282 B2 | 11/2013 | Angle et al. |
| 8,588,464 B2 | 11/2013 | Albertson et al. |
| 8,588,972 B2 | 11/2013 | Fung |
| 8,591,412 B2 | 11/2013 | Kovarik et al. |
| 8,594,935 B2 | 11/2013 | Cioffi et al. |
| 8,606,316 B2 | 12/2013 | Evanitsky |
| 8,610,879 B2 | 12/2013 | Ben-Moshe et al. |
| 8,630,633 B1 | 1/2014 | Tedesco et al. |
| 8,676,274 B2 | 3/2014 | Li |
| 8,676,623 B2 | 3/2014 | Gale et al. |
| 8,694,251 B2 | 4/2014 | Janardhanan et al. |
| 8,704,902 B2 | 4/2014 | Naick et al. |
| 8,718,672 B2 | 5/2014 | Xie et al. |
| 8,743,145 B1 | 6/2014 | Price |
| 8,750,898 B2 | 6/2014 | Haney |
| 8,768,071 B2 | 7/2014 | Tsuchinaga et al. |
| 8,786,680 B2 | 7/2014 | Shiratori et al. |
| 8,797,141 B2 | 8/2014 | Best et al. |
| 8,797,386 B2 | 8/2014 | Chou et al. |
| 8,803,699 B2 | 8/2014 | Foshee et al. |
| 8,805,929 B2 | 8/2014 | Erol et al. |
| 8,812,244 B2 | 8/2014 | Angelides |
| 8,814,019 B2 | 8/2014 | Dyster et al. |
| 8,825,398 B2 | 9/2014 | Alexandre et al. |
| 8,836,532 B2 | 9/2014 | Fish, Jr. et al. |
| 8,836,580 B2 | 9/2014 | Mendelson |
| 8,836,910 B2 | 9/2014 | Cashin et al. |
| 8,902,303 B2 | 12/2014 | Na'Aman et al. |
| 8,909,534 B1 | 12/2014 | Heath |
| D721,673 S | 1/2015 | Park et al. |
| 8,926,330 B2 | 1/2015 | Taghavi |
| 8,930,458 B2 | 1/2015 | Lewis et al. |
| 8,981,682 B2 | 3/2015 | Delson et al. |
| 8,994,498 B2 | 3/2015 | Agrafioti |
| D727,194 S | 4/2015 | Wilson |
| 9,004,330 B2 | 4/2015 | White |
| 9,025,016 B2 | 5/2015 | Wexler et al. |
| 9,042,596 B2 | 5/2015 | Connor |
| 9,053,094 B2 | 6/2015 | Yassa |
| 9,076,450 B1 | 7/2015 | Sadek |
| 9,081,079 B2 | 7/2015 | Chao et al. |
| 9,081,385 B1 | 7/2015 | Ferguson et al. |
| D736,741 S | 8/2015 | Katz |
| 9,111,545 B2 | 8/2015 | Jadhav et al. |
| D738,238 S | 9/2015 | Pede et al. |
| 9,137,484 B2 | 9/2015 | DiFrancesco et al. |
| 9,137,639 B2 | 9/2015 | Garin et al. |
| 9,140,554 B2 | 9/2015 | Jerauld |

(56) References Cited

U.S. PATENT DOCUMENTS

| | | |
|---|---|---|
| 9,148,191 B2 | 9/2015 | Teng et al. |
| 9,158,378 B2 | 10/2015 | Hirukawa |
| D742,535 S | 11/2015 | Wu |
| D743,933 S | 11/2015 | Park et al. |
| 9,185,489 B2 | 11/2015 | Gerber et al. |
| 9,190,058 B2 | 11/2015 | Klein |
| 9,104,806 B2 | 12/2015 | Stivoric et al. |
| 9,230,430 B2 | 1/2016 | Civelli et al. |
| 9,232,366 B1 | 1/2016 | Charlier et al. |
| 9,267,801 B2 | 2/2016 | Gupta et al. |
| 9,269,015 B2 | 2/2016 | Boncyk et al. |
| 9,275,376 B2 | 3/2016 | Barraclough et al. |
| 9,304,588 B2 | 4/2016 | Aldossary |
| D756,958 S | 5/2016 | Lee et al. |
| D756,959 S | 5/2016 | Lee et al. |
| 9,335,175 B2 | 5/2016 | Zhang et al. |
| 9,341,014 B2 | 5/2016 | Oshima et al. |
| 9,355,547 B2 | 5/2016 | Stevens et al. |
| D769,453 S * | 10/2016 | Ma .............................. D24/215 |
| 9,576,460 B2 * | 2/2017 | Dayal .................... G08B 21/02 |
| 9,578,307 B2 * | 2/2017 | Moore ............... H04N 13/0239 |
| 2001/0023387 A1 | 9/2001 | Rollo |
| 2002/0067282 A1 | 6/2002 | Moskowitz et al. |
| 2002/0071277 A1 | 6/2002 | Starner et al. |
| 2002/0075323 A1 | 6/2002 | O'Dell |
| 2002/0173346 A1 | 11/2002 | Wang |
| 2002/0178344 A1 | 11/2002 | Bourguet |
| 2003/0026461 A1 | 2/2003 | Arthur Hunter |
| 2003/0133008 A1 | 7/2003 | Stephenson |
| 2003/0133085 A1 | 7/2003 | Tretiakoff |
| 2003/0179133 A1 | 9/2003 | Pepin et al. |
| 2004/0056907 A1 | 3/2004 | Sharma |
| 2004/0232179 A1 | 11/2004 | Chauhan |
| 2004/0267442 A1 | 12/2004 | Fehr et al. |
| 2005/0020845 A1 | 9/2005 | Fink et al. |
| 2005/0221260 A1 | 10/2005 | Kikuchi |
| 2005/0259035 A1 | 11/2005 | Iwaki |
| 2005/0283752 A1 | 12/2005 | Fruchter |
| 2006/0004512 A1 | 1/2006 | Herbst et al. |
| 2006/0028550 A1 | 2/2006 | Palmer, Jr. et al. |
| 2006/0029256 A1 | 2/2006 | Miyoshi et al. |
| 2006/0129308 A1 | 6/2006 | Kates |
| 2006/0171704 A1 | 8/2006 | Bingle et al. |
| 2006/0177086 A1 | 8/2006 | Rye et al. |
| 2006/0184318 A1 | 8/2006 | Yoshimine |
| 2006/0292533 A1 | 12/2006 | Selod |
| 2007/0001904 A1 | 1/2007 | Mendelson |
| 2007/0052672 A1 | 3/2007 | Ritter et al. |
| 2007/0173688 A1 | 7/2007 | Kim |
| 2007/0182812 A1 | 8/2007 | Ritchey |
| 2007/0202865 A1 | 8/2007 | Moride |
| 2007/0230786 A1 | 10/2007 | Foss |
| 2007/0296572 A1 | 12/2007 | Fein et al. |
| 2008/0024594 A1 | 1/2008 | Ritchey |
| 2008/0068559 A1 | 3/2008 | Howell et al. |
| 2008/0120029 A1 | 5/2008 | Zelek et al. |
| 2008/0144854 A1 | 6/2008 | Abreu |
| 2008/0145822 A1 | 6/2008 | Bucchieri |
| 2008/0174676 A1 | 7/2008 | Squilla et al. |
| 2008/0198222 A1 | 8/2008 | Gowda |
| 2008/0198324 A1 | 8/2008 | Fuziak |
| 2008/0208455 A1 | 8/2008 | Hartman |
| 2008/0251110 A1 | 10/2008 | Pede |
| 2008/0260210 A1 | 10/2008 | Kobeli |
| 2009/0012788 A1 | 1/2009 | Gilbert |
| 2009/0040215 A1 | 2/2009 | Afzulpurkar |
| 2009/0058611 A1 | 3/2009 | Kawamura |
| 2009/0106016 A1 | 4/2009 | Athsani |
| 2009/0118652 A1 | 5/2009 | Carlucci |
| 2009/0122161 A1 | 5/2009 | Bolkhovitinov |
| 2009/0122648 A1 | 5/2009 | Mountain et al. |
| 2009/0157302 A1 | 6/2009 | Tashev et al. |
| 2009/0177437 A1 | 7/2009 | Roumeliotis |
| 2009/0189974 A1 | 7/2009 | Deering |
| 2009/0210596 A1 | 8/2009 | Furuya |
| 2010/0041378 A1 | 2/2010 | Aceves et al. |
| 2010/0080418 A1 | 4/2010 | Ito |
| 2010/0109918 A1 | 5/2010 | Liebermann |
| 2010/0110368 A1 | 5/2010 | Chaum |
| 2010/0179452 A1 | 7/2010 | Srinivasan |
| 2010/0182242 A1 | 7/2010 | Fields et al. |
| 2010/0182450 A1 | 7/2010 | Kumar et al. |
| 2010/0198494 A1 | 8/2010 | Chao et al. |
| 2010/0199232 A1 | 8/2010 | Mistry et al. |
| 2010/0241350 A1 | 9/2010 | Cioffi et al. |
| 2010/0245585 A1 | 9/2010 | Fisher et al. |
| 2010/0267276 A1 | 10/2010 | Wu et al. |
| 2010/0292917 A1 | 11/2010 | Emam et al. |
| 2010/0298976 A1 | 11/2010 | Sugihara et al. |
| 2010/0305845 A1 | 12/2010 | Alexandre et al. |
| 2010/0308999 A1 | 12/2010 | Chornenky |
| 2011/0066383 A1 | 3/2011 | Jangle et al. |
| 2011/0071830 A1 | 3/2011 | Kim |
| 2011/0092249 A1 | 4/2011 | Evanitsky |
| 2011/0124383 A1 | 5/2011 | Garra et al. |
| 2011/0125735 A1 | 5/2011 | Petrou |
| 2011/0181422 A1 | 7/2011 | Tran |
| 2011/0187640 A1 | 8/2011 | Jacobsen et al. |
| 2011/0211760 A1 | 9/2011 | Boncyk et al. |
| 2011/0216006 A1 | 9/2011 | Litschel |
| 2011/0221670 A1 | 9/2011 | King, III et al. |
| 2011/0234584 A1 | 9/2011 | Endo |
| 2011/0246064 A1 | 10/2011 | Nicholson |
| 2011/0260681 A1 | 10/2011 | Guccione et al. |
| 2011/0307172 A1 | 12/2011 | Jadhav et al. |
| 2012/0016578 A1 | 1/2012 | Coppens |
| 2012/0053826 A1 | 3/2012 | Slamka |
| 2012/0062357 A1 | 3/2012 | Slamka |
| 2012/0069511 A1 | 3/2012 | Azera |
| 2012/0075168 A1 | 3/2012 | Osterhout et al. |
| 2012/0082962 A1 | 4/2012 | Schmidt |
| 2012/0085377 A1 | 4/2012 | Trout |
| 2012/0092161 A1 | 4/2012 | West |
| 2012/0092460 A1 | 4/2012 | Mahoney |
| 2012/0123784 A1 | 5/2012 | Baker et al. |
| 2012/0136666 A1 | 5/2012 | Corpier et al. |
| 2012/0143495 A1 | 6/2012 | Dantu |
| 2012/0162423 A1 | 6/2012 | Xiao et al. |
| 2012/0194552 A1 | 8/2012 | Osterhout et al. |
| 2012/0206335 A1 | 8/2012 | Osterhout et al. |
| 2012/0206607 A1 | 8/2012 | Morioka |
| 2012/0207356 A1 | 8/2012 | Murphy |
| 2012/0214418 A1 | 8/2012 | Lee et al. |
| 2012/0220234 A1 | 8/2012 | Abreu |
| 2012/0232430 A1 | 9/2012 | Boissy et al. |
| 2012/0249797 A1 | 10/2012 | Haddick et al. |
| 2012/0252483 A1 | 10/2012 | Farmer et al. |
| 2012/0316884 A1 | 12/2012 | Rozaieski et al. |
| 2012/0323485 A1 | 12/2012 | Mutoh |
| 2012/0327194 A1 | 12/2012 | Shiratori |
| 2013/0002452 A1 | 1/2013 | Lauren |
| 2013/0044005 A1 | 2/2013 | Foshee et al. |
| 2013/0046541 A1 | 2/2013 | Klein et al. |
| 2013/0066636 A1 | 3/2013 | Singhal |
| 2013/0079061 A1 | 3/2013 | Jadhav |
| 2013/0090133 A1 | 4/2013 | D'Jesus Bencci |
| 2013/0115578 A1 | 5/2013 | Shiina |
| 2013/0115579 A1 | 5/2013 | Taghavi |
| 2013/0116559 A1 | 5/2013 | Levin et al. |
| 2013/0127980 A1 | 5/2013 | Haddick |
| 2013/0128051 A1 | 5/2013 | Velipasalar et al. |
| 2013/0131985 A1 | 5/2013 | Weiland et al. |
| 2013/0141576 A1 | 6/2013 | Lord et al. |
| 2013/0144629 A1 | 6/2013 | Johnston |
| 2013/0145531 A1 * | 6/2013 | Fratesi ............... A41D 13/0512 2/462 |
| 2013/0155474 A1 | 6/2013 | Roach et al. |
| 2013/0157230 A1 | 6/2013 | Morgan |
| 2013/0184982 A1 | 7/2013 | DeLuca et al. |
| 2013/0201344 A1 | 8/2013 | Sweet, III |
| 2013/0202274 A1 | 8/2013 | Chan |
| 2013/0204605 A1 | 8/2013 | Illgner-Fehns |
| 2013/0211718 A1 | 8/2013 | Yoo et al. |
| 2013/0218456 A1 | 8/2013 | Zelek et al. |

(56) References Cited

U.S. PATENT DOCUMENTS

| | | |
|---|---|---|
| 2013/0228615 A1 | 9/2013 | Gates et al. |
| 2013/0229669 A1 | 9/2013 | Smits |
| 2013/0243250 A1 | 9/2013 | France |
| 2013/0245396 A1 | 9/2013 | Berman et al. |
| 2013/0250078 A1 | 9/2013 | Levy |
| 2013/0250233 A1 | 9/2013 | Blum et al. |
| 2013/0253818 A1 | 9/2013 | Sanders et al. |
| 2013/0265450 A1 | 10/2013 | Barnes, Jr. |
| 2013/0271584 A1 | 10/2013 | Wexler et al. |
| 2013/0290909 A1 | 10/2013 | Gray |
| 2013/0307842 A1 | 11/2013 | Grinberg et al. |
| 2013/0311179 A1 | 11/2013 | Wagner |
| 2013/0328683 A1 | 12/2013 | Sitbon et al. |
| 2013/0332452 A1 | 12/2013 | Jarvis |
| 2014/0009561 A1 | 1/2014 | Sutherland et al. |
| 2014/0031081 A1 | 1/2014 | Vossoughi et al. |
| 2014/0031977 A1 | 1/2014 | Goldenberg et al. |
| 2014/0032596 A1 | 1/2014 | Fish et al. |
| 2014/0037149 A1 | 2/2014 | Zetune |
| 2014/0055353 A1 | 2/2014 | Takahama |
| 2014/0071234 A1 | 3/2014 | Millett |
| 2014/0081631 A1 | 3/2014 | Zhu et al. |
| 2014/0085446 A1 | 3/2014 | Hicks |
| 2014/0098018 A1 | 4/2014 | Kim et al. |
| 2014/0100773 A1 | 4/2014 | Cunningham et al. |
| 2014/0125700 A1 | 5/2014 | Ramachandran et al. |
| 2014/0132388 A1 | 5/2014 | Alalawi |
| 2014/0133290 A1 | 5/2014 | Yokoo |
| 2014/0160250 A1 | 6/2014 | Pomerantz |
| 2014/0184384 A1 | 7/2014 | Zhu et al. |
| 2014/0184775 A1 | 7/2014 | Drake |
| 2014/0204245 A1 | 7/2014 | Wexler |
| 2014/0222023 A1 | 8/2014 | Kim et al. |
| 2014/0233859 A1 | 8/2014 | Cho |
| 2014/0236932 A1 | 8/2014 | Ikonomov |
| 2014/0249847 A1 | 9/2014 | Soon-Shiong |
| 2014/0251396 A1 | 9/2014 | Subhashrao et al. |
| 2014/0253702 A1 | 9/2014 | Wexler et al. |
| 2014/0278070 A1 | 9/2014 | McGavran et al. |
| 2014/0281943 A1 | 9/2014 | Prilepov |
| 2014/0287382 A1 | 9/2014 | Villar Cloquell |
| 2014/0309806 A1 | 10/2014 | Ricci |
| 2014/0313040 A1 | 10/2014 | Wright, Sr. |
| 2014/0335893 A1 | 11/2014 | Ronen |
| 2014/0343846 A1 | 11/2014 | Goldman et al. |
| 2014/0345956 A1 | 11/2014 | Kojina |
| 2014/0347265 A1 | 11/2014 | Aimone |
| 2014/0368412 A1 | 12/2014 | Jacobsen et al. |
| 2014/0369541 A1 | 12/2014 | Miskin et al. |
| 2014/0379251 A1 | 12/2014 | Tolstedt |
| 2014/0379336 A1 | 12/2014 | Bhatnager |
| 2015/0002808 A1 | 1/2015 | Rizzo, III et al. |
| 2015/0016035 A1 | 1/2015 | Tussy |
| 2015/0058237 A1 | 2/2015 | Bailey |
| 2015/0063661 A1 | 3/2015 | Lee |
| 2015/0081884 A1 | 3/2015 | Maguire |
| 2015/0099946 A1 | 4/2015 | Sahin |
| 2015/0109107 A1 | 4/2015 | Gomez et al. |
| 2015/0120186 A1 | 4/2015 | Heikes |
| 2015/0125831 A1 | 5/2015 | Chandrashekhar Nair et al. |
| 2015/0135310 A1 | 5/2015 | Lee |
| 2015/0141085 A1 | 5/2015 | Nuovo et al. |
| 2015/0142891 A1 | 5/2015 | Haque et al. |
| 2015/0154643 A1 | 6/2015 | Artman et al. |
| 2015/0196101 A1* | 7/2015 | Dayal .................. G01C 21/206 63/1.11 |
| 2015/0198454 A1 | 7/2015 | Moore et al. |
| 2015/0198455 A1 | 7/2015 | Chen et al. |
| 2015/0199566 A1 | 7/2015 | Moore et al. |
| 2015/0201181 A1 | 7/2015 | Moore et al. |
| 2015/0211858 A1 | 7/2015 | Jerauld |
| 2015/0219757 A1 | 8/2015 | Boelter et al. |
| 2015/0223355 A1 | 8/2015 | Fleck |
| 2015/0256977 A1 | 9/2015 | Huang |
| 2015/0257555 A1 | 9/2015 | Wong |
| 2015/0260474 A1 | 9/2015 | Rublowsky et al. |
| 2015/0262509 A1 | 9/2015 | Labbe |
| 2015/0279172 A1 | 10/2015 | Hyde |
| 2015/0324646 A1 | 11/2015 | Kimia |
| 2015/0330787 A1 | 11/2015 | Cioffi et al. |
| 2015/0336276 A1 | 11/2015 | Song et al. |
| 2015/0338917 A1 | 11/2015 | Steiner et al. |
| 2015/0341591 A1 | 11/2015 | Kelder et al. |
| 2015/0346496 A1 | 12/2015 | Haddick et al. |
| 2015/0356345 A1 | 12/2015 | Velozo |
| 2015/0356837 A1 | 12/2015 | Pajestka et al. |
| 2015/0364943 A1 | 12/2015 | Vick et al. |
| 2015/0367176 A1 | 12/2015 | Bejestan |
| 2015/0375395 A1 | 12/2015 | Kwon et al. |
| 2016/0007158 A1 | 1/2016 | Venkatraman |
| 2016/0028917 A1 | 1/2016 | Wexler |
| 2016/0042228 A1 | 2/2016 | Opalka |
| 2016/0078289 A1 | 3/2016 | Michel |
| 2016/0085278 A1* | 3/2016 | Osterhout ............... G06F 1/206 361/679.03 |
| 2016/0098138 A1 | 4/2016 | Park |
| 2016/0156850 A1 | 6/2016 | Werblin et al. |
| 2016/0198319 A1 | 7/2016 | Huang |
| 2016/0350514 A1 | 12/2016 | Rajendran |

FOREIGN PATENT DOCUMENTS

| | | |
|---|---|---|
| CN | 201440733 | 4/2010 |
| CN | 101803988 | 8/2010 |
| CN | 101647745 | 1/2011 |
| CN | 102316193 | 1/2012 |
| CN | 102631280 | 8/2012 |
| CN | 202547659 | 11/2012 |
| CN | 202722736 | 2/2013 |
| CN | 102323819 | 6/2013 |
| CN | 103445920 | 12/2013 |
| DE | 102011080056 | 1/2013 |
| DE | 102012000587 | 7/2013 |
| DE | 102012202614 | 8/2013 |
| EP | 1174049 | 9/2004 |
| EP | 1721237 | 11/2006 |
| EP | 2368455 | 9/2011 |
| EP | 2371339 | 10/2011 |
| EP | 2127033 | 8/2012 |
| EP | 2581856 | 4/2013 |
| EP | 2751775 | 7/2016 |
| FR | 2885251 | 11/2006 |
| GB | 2401752 | 11/2004 |
| JP | 1069539 | 3/1998 |
| JP | 2001304908 | 10/2001 |
| JP | 2010012529 | 1/2010 |
| JP | 2010182193 | 8/2010 |
| JP | 4727352 | 7/2011 |
| JP | 2013169611 | 9/2013 |
| KR | 100405636 | 11/2003 |
| KR | 20080080688 | 9/2008 |
| KR | 20120020212 | 3/2012 |
| KR | 1250929 | 4/2013 |
| WO | WO 1995004440 | 2/1995 |
| WO | WO 9949656 | 9/1999 |
| WO | WO 0010073 | 2/2000 |
| WO | WO 0038393 | 6/2000 |
| WO | WO 179956 | 10/2001 |
| WO | WO 2004/076974 | 9/2004 |
| WO | WO 2006/028354 | 3/2006 |
| WO | WO 2006/045819 | 5/2006 |
| WO | WO 2007/031782 | 3/2007 |
| WO | WO 2008015375 | 2/2008 |
| WO | WO 2008/035993 | 3/2008 |
| WO | WO 2008/008791 | 4/2008 |
| WO | WO 2008/096134 | 8/2008 |
| WO | WO 2008127316 | 10/2008 |
| WO | WO 2010/062481 | 6/2010 |
| WO | WO 2010/109313 | 9/2010 |
| WO | WO 2012/040703 | 3/2012 |
| WO | WO 2012163675 | 12/2012 |
| WO | WO 2013/045557 | 4/2013 |
| WO | WO 2013/054257 | 4/2013 |
| WO | WO 2013/067539 | 5/2013 |

(56) References Cited

FOREIGN PATENT DOCUMENTS

| WO | WO 2013/147704 | 10/2013 |
|---|---|---|
| WO | WO 2014104531 | 7/2014 |
| WO | WO 2014/138123 | 9/2014 |
| WO | WO 2014/172378 | 10/2014 |
| WO | WO 2015065418 | 5/2015 |
| WO | WO 2015092533 | 6/2015 |
| WO | WO 2015108882 | 7/2015 |
| WO | WO 2015127062 | 8/2015 |

OTHER PUBLICATIONS

Diallo, Amadou; Sep. 18, 2014; Apple iOS8: Top New Features, Forbes Magazine.
N. Kalar, T. Lawers, D. Dewey, T. Stepleton, M.B. Dias; Iterative Design of a Braille Writing Tutor to Combat Illiteracy; Aug. 30, 2007; IEEE.
AlZuhair et al.; "NFC Based Applications for Visually Impaired People—A Review"; IEEE International Conference on Multimedia and Expo Workshops (ICMEW), Jul. 14, 2014; 7 pages.
"Light Detector" EveryWare Technologies; 2 pages; Jun. 18, 2016.
Aggarwal et al.; "All-in-One Companion for Visually Impaired;" International Journal of Computer Applications; vol. 79, No. 14; pp. 37-40; Oct. 2013.
AppleVis; An Introduction to Braille Screen Input on iOS 8; http://www.applevis.com/guides/braille-ios/introduction-braille-screen-input-ios-8, Nov. 16, 2014; 7 pages.
Arati et al. "Object Recognition in Mobile Phone Application for Visually Impaired Users;" IOSR Journal of Computer Engineering (IOSR-JCE); vol. 17, Impaired No. 1; pp. 30-33; Jan. 2015.
Bharathi et al.; "Effective Navigation for Visually Impaired by Wearable Obstacle Avoidance System;" 2012 International Conference on Computing, Electronics and Electrical Technologies (ICCEET); pp. 956-958; 2012.
Bhatlawande et al.; "Way-finding Electronic Bracelet for Visually Impaired People"; IEEE Point-of-Care Healthcare Technologies (PHT), Jan. 16-18, 2013; 4 pages.
Bigham et al.; "VizWiz: Nearly Real-Time Answers to Visual Questions" Proceedings of the 23nd annual ACM symposium on User interface software and technology; 2010; 2 pages.
Blaze Engineering; "Visually Impaired Resource Guide: Assistive Technology for Students who use Braille"; Braille 'n Speak Manual; http://www.blaize.com; Nov. 17, 2014; 5 pages.
Blenkhorn et al.; "An Ultrasonic Mobility Device with Minimal Audio Feedback"; Center on Disabilities Technology and Persons with Disabilities Conference; Nov. 22, 1997; 5 pages.
Borenstein et al.; "The GuideCane—A Computerized Travel Aid for the Active Guidance of Blind Pedestrians"; IEEE International Conference on Robotics and Automation; Apr. 21-27, 1997; 6 pages.
Bujacz et al.; "Remote Guidance for the Blind—A Proposed Teleassistance System and Navigation Trials"; Conference on Human System Interactions; May 25-27, 2008; 6 pages.
Burbey et al.; "Human Information Processing with the Personal Memex"; ISE 5604 Fall 2005; Dec. 6, 2005; 88 pages.
Campos et al.; "Design and Evaluation of a Spoken-Feedback Keyboard"; Department of Information Systems and Computer Science, INESC-ID/IST/Universidade Tecnica de Lisboa, Jul. 2004; 6 pages.
Caperna et al.; "A Navigation and Object Location Device for the Blind"; Tech. rep. University of Maryland College Park; May 2009; 129 pages.
Cardonha et al.; "A Crowdsourcing Platform for the Construction of Accessibility Maps"; W4A'13 Proceedings of the 10th International Cross-Disciplinary Conference on Web Accessibility; Article No. 26; 2013; 5 pages.
Chaudary et al.; "Alternative Navigation Assistance Aids for Visually Impaired Blind Persons"; Proceedings of ICEAPVI; Feb. 12-14, 2015; 5 pages.
Coughlan et al.; "Crosswatch: A System for Providing Guidance to Visually Impaired Travelers at Traffic Intersections"; Journal of Assistive Technologies 7.2; 2013; 17 pages.
D'Andrea, Frances Mary; "More than a Perkins Brailler: A Review of the Mountbatten Brailler, Part 1"; AFB AccessWorld Magazine; vol. 6, No. 1, Jan. 2005; 9 pages.
Dias et al.; "Enhancing an Automated Braille Writing Tutor"; IEEE/RSJ International Conference on Intelligent Robots and Systems; Oct. 11-15, 2009; 7 pages.
Dowling et al.; "Intelligent Image Processing Constraints for Blind Mobility Facilitated Through Artificial Vision"; 8th Australian and NewZealand Intelligent Information Systems Conference (ANZIIS); Dec. 10-12, 2003; 7 pages.
Ebay; MATIN (Made in Korea) Neoprene Canon DSLR Camera Curved Neck Strap #6782; http://www.ebay.com/itm/MATIN-Made-in-Korea-Neoprene-Canon-DSLR-Camera-Curved-Neck-Strap-6782-/281608526018?hash=item41912d18c2:g:~pMAAOSwe-FU6zDa ; 4 pages.
Eccles, Lisa; "Smart Walker Detects Obstacles"; Electronic Design; http://electronicdesign.com/electromechanical/smart-walker-detects-obstaeles; Aug. 20, 2001; 2 pages.
Frizera et al.; "The Smart Walkers as Geriatric Assistive Device. The SIMBIOSIS Purpose"; Gerontechnology, vol. 7, No. 2; Jan. 30, 2008; 6 pages.
Garaj et al.; "A System for Remote Sighted Guidance of Visually Impaired Pedestrians"; The British Journal of Visual. Impairment; vol. 21, No. 2, 2003; 9 pages.
Ghiani, et al.; "Vibrotactile Feedback to Aid Blind Users of Mobile Guides"; Journal of Visual Languages and Computing 20; 2009; 13 pages.
Glover et al.; "A Robotically-Augmented Walker for Older Adults"; Carnegie Mellon University, School of Computer Science; Aug. 1, 2003; 13 pages.
Graf, Christian; "Verbally Annotated Tactile Maps—Challenges and Approaches"; Spatial Cognition VII, vol. 6222; Aug. 15-19, 2010; 16 pages.
Graft, Birgit; "An Adaptive Guidance System for Robotic Walking Aids"; Journal of Computing and Information Technology—CIT 17; 2009; 12 pages.
Greenberg et al.; "Finding Your Way: A Curriculum for Teaching and Using the Braillenote with Sendero GPS 2011"; California School for the Blind; 2011; 190 pages.
Guerrero et al.; "An Indoor Navigation System for the Visually Impaired"; Sensors vol. 12, Issue 6; Jun. 13, 2012; 23 pages.
Guy et al; "CrossingGuard: Exploring Information Content in Navigation Aids for Visually Impaired Pedestrians" Proceedings of the SIGCHI Conference on Human Factors in Computing Systems; May 5-10, 2012; 10 pages.
Hamid, Nazatul Naquiah Abd; "Facilitating Route Learning Using Interactive Audio-Tactile Maps for Blind and Visually Impaired People"; CHI 2013 Extended Abstracts; Apr. 27, 2013; 6 pages.
Helal et al.; "Drishti: An Integrated Navigation System for Visually Impaired and Disabled"; Fifth International Symposium on Wearable Computers; Oct. 8-9, 2001; 8 pages.
Hesch et al.; "Design and Analysis of a Portable Indoor Localization Aid for the Visually Impaired"; International Journal of Robotics Research; vol. 29; Issue 11; Sep. 2010; 15 pgs.
Heyes, Tony; "The Sonic Pathfinder an Electronic Travel Aid for the Vision Impaired"; http://members.optuszoo.com.au/aheyew40/pa/pf_blerf.html; Dec. 11, 2014; 7 pages.
Joseph et al.; "Visual Semantic Parameterization—To Enhance Blind User Perception for Indoor Navigation"; Multimedia and Expo Workshops (ICMEW), 2013 IEEE International Conference; Jul. 15, 2013; 7 pages.
Kalra et al.; "A Braille Writing Tutor to Combat Illiteracy in Developing Communities"; Carnegie Mellon University Research Showcase, Robotics Institute; 2007; 10 pages.
Kammoun et al.; "Towards a Geographic Information System Facilitating Navigation of Visually Impaired Users"; Springer Berlin Heidelberg; 2012; 8 pages.
Katz et al; "NAVIG: Augmented Reality Guidance System for the Visually Impaired"; Virtual Reality (2012) vol. 16; 2012; 17 pages.

(56) References Cited

OTHER PUBLICATIONS

Kayama et al.; "*Outdoor Environment Recognition and Semi-Autonomous Mobile Vehicle for Supporting Mobility of the Elderly and Disabled People*"; National Institute of Information and Communications Technology, vol. 54, No. 3; Aug. 2007; 11 pages.

Kirinic et al.; "*Computers in Education of Children with Intellectual and Related Developmental Disorders*"; International Journal of Emerging Technologies in Learning, vol. 5, 2010, 5 pages.

Krishna et al.; "*A Systematic Requirements Analysis and Development of an Assistive Device to Enhance the Social Interaction of People Who are Blind or Visually Impaired*"; Workshop on Computer Vision Applications for the Visually Impaired; Marseille, France; 2008; 12 pages.

Kumar et al.; "*An Electronic Travel Aid for Navigation of Visually Impaired Persons*"; Communications Systems and Networks (COMSNETS), 2011 Third International Conference; Jan. 2011; 5 pages.

Lee et al.; "*Adaptive Power Control of Obstacle Avoidance System Using via Motion Context for Visually Impaired Person.*" International Conference on Cloud Computing and Social Networking (ICCCSN), Apr. 26-27, 2012 4 pages.

Lee et al.; "*A Walking Guidance System for the Visually Impaired*"; International Journal of Pattern Recognition and Artificial Intelligence; vol. 22; No. 6; 2008; 16 pages.

Mann et al.; "*Blind Navigation with a Wearable Range Camera and Vibrotactile Helmet*"; 19th ACM International Conference on Multimedia; Nov. 28, 2011; 4 pages.

Mau et al.; "BlindAid: An Electronic Travel Aid for the Bling;" *The Robotics Institute Carnegie Mellon University*; 27 pages; May 2008.

Meijer, Dr. Peter B.L.; "*Mobile OCR, Face and Object Recognition for the Blind*"; The vOICe, www.seeingwithsound.com/ocr.htm; Apr. 18, 2014; 7 pages.

Merino-Garcia, et al.; "*A Head-Mounted Device for Recognizing Text in Natural Sciences*"; CBDAR'11 Proceedings of the 4th International Conference on Camera-Based Document Analysis and Recognition; Sep. 22, 2011; 7 pages.

Merri et al.; "*The Instruments for a Blind Teacher of English: The challenge of the board*"; European Journal of Psychology of Education, vol. 20, No. 4 (Dec. 2005), 15 pages.

NEWEGG; Motorola Behind the Neck Stereo Bluetooth Headphone Black/Red Bulk (S9)—OEM; http://www.newegg.com/Product/Product.aspx?Item=N82E16875982212&Tpk=n82e16875982212 3 pages.

NEWEGG; Motorola S10-HD Bluetooth Stereo Headphone w/ Comfortable Sweat Proof Design; http://www.newegg.com/Product/Product.aspx?Item=9SIA0NW2G39901&Tpk=9sia0nw2g39901; 4 pages.

Nordin et al.; "*Indoor Navigation and Localization for Visually Impaired People Using Weighted Topological Map*"; Journal of Computer Science vol. 5, Issue 11; 2009; 7 pages.

OMRON; Optical Character Recognition Sensor User's Manual; 2012; 450 pages.

OrCam; www.orcam.com; Jul. 22, 2014; 3 pages.

Pagliarini et al.; "*Robotic Art for Wearable*"; Proceedings of EUROSIAM: European Conference for the Applied Mathematics and Informatics 2010; 10 pages.

Paladugu et al.; "*GoingEasy® with Crowdsourcing in the Web 2.0 World for Visually Impaired Users: Design and User Study*"; Arizona State University; 8 pages.

Park, Sungwoo; "*Voice Stick*"; www.yankodesign.com/2008/08/21/voice-stick; Aug. 21, 2008; 4 pages.

Parkes, Don; "*Audio Tactile Systems for Designing and Learning Complex Environments as a Vision Impaired Person: Static and Dynamic Spatial Information Access*"; EdTech-94 Proceedings; 1994; 8 pages.

Pawar et al.; "*Multitasking Stick for Indicating Safe Path to Visually Disable People*"; IOSR Journal of Electronics and Communication Engineering (IOSR-JECE), vol. 10, Issue 3, Ver. II; May-Jun. 2015; 5 pages.

Pawar et al.; "Review Paper on Multitasking Stick for Guiding Safe Path for Visually Disable People;" *IJPRET*; vol. 3, No. 9; pp. 929-936; 2015.

Ram et al.; "The People Sensor: A Mobility Aid for the Visually Impaired;" 2012 16th International Symposium on Wearable Computers; pp. 166-167; 2012.

Ramya, et al.; "*Voice Assisted Embedded Navigation System for the Visually Impaired*"; International Journal of Computer Applications; vol. 64, No. 13, Feb. 2013; 7 pages.

Ran et al.; "*Drishti: An Integrated Indoor/Outdoor Blind Navigation System and Service*"; Proceeding PERCOM '04 Proceedings of the Second IEEE International Conference on Pervasive Computing and Communications (PerCom'04); 2004; 9 pages.

Rentschler et al.; "*Intelligent Walkers for the Elderly: Performance and Safety Testing of VA-PAMAID Robotic Walker*"; Department of Veterans Affairs Journal of Rehabilitation Research and Development; vol. 40, No. 5; Sep./Oct. 2013; 9pages.

Rodríguez et al.; "*Assisting the Visually Impaired: Obstacle Detection and Warning System by Acoustic Feedback*"; Sensors 2012; vol. 12; 21 pages.

Rodriguez et al; "*CrowdSight: Rapidly Prototyping Intelligent Visual Processing Apps*"; AAAI Human Computation Workshop (HCOMP); 2011; 6 pages.

Rodriquez-Losada et al.; "*Guido, The Robotic Smart Walker for the Frail Visually Impaired*"; IEEE International Conference on Robotics and Automation (ICRA); Apr. 18-22, 2005; 15 pages.

Science Daily; "*Intelligent Walker Designed to Assist the Elderly and People Undergoing Medical Rehabilitation*"; http://www.sciencedaily.com/releases/2008/11/081107072015.htm; Jul. 22, 2014; 4 pages.

Shoval et al.; "*Navbelt and the Guidecane—Robotics-Based Obstacle-Avoidance Systems for the Blind and Visually Impaired*"; IEEE Robotics & Automation Magazine, vol. 10, Issue 1; Mar. 2003; 12 pages.

Shoval et al.; "*The Navbelt—A Computerized Travel Aid for the Blind*"; RESNA Conference, Jun. 12-17, 1993; 6 pages.

Singhal; "The Development of an Intelligent Aid for Blind and Old People;" *Emerging Trends and Applications in Computer Science (ICETACS), 2013 1st International Conference*; pp. 182-185; Sep. 13, 2013.

Sudol et al.; "*LookTel—A Comprehensive Platform for Computer-Aided Visual Assistance*"; Computer Vision and Pattern Recognition Workshops (CVPRW), 2010 IEEE Computer Society Conference; Jun. 13-18, 2010; 8 pages.

The Nex Band; http://www.mightycast.com/#faq; May 19, 2015; 4 pages.

Treuillet; "*Outdoor/Indoor Vision-Based Localization for Blind Pedestrian Navigation Assistance*"; WSPC/Instruction File; May 23, 2010; 16 pages.

Trinh et al.; "*Phoneme-based Predictive Text Entry Interface*"; Proceedings of the 16th International ACM SIGACCESS Conference on Computers & Accessibility; Oct. 2014; 2 pgs.

Wang, et al.; "*Camera-Based Signage Detection and Recognition for Blind Persons*"; 13th International Conference (ICCHP) Part 2 Proceedings; Jul. 11-13, 2012; 9 pages.

Ward et al.; "*Visual Experiences in the Blind Induced by an Auditory Sensory Substitution Device*"; Journal of Consciousness and Cognition; Oct. 2009; 30 pages.

Wilson, Jeff, et al. "*Swan: System for Wearable Audio Navigation*"; 11th IEEE International Symposium on Wearable Computers; Oct. 11-13, 2007; 8 pages.

Yabu et al.; "Development of a Wearable Haptic Tactile Interface as an Aid for the Hearing and/or Visually Impaired;" *NTUT Education of Disabilities*; vol. 13; pp. 5-12; 2015.

Yang, et al.; "*Towards Automatic Sign Translation*"; The Interactive Systems Lab, Carnegie Mellon University; 2001; 5 pages.

Yi, Chucai; "*Assistive Text Reading from Complex Background for Blind Persons*"; CBDAR'11 Proceedings of the 4th International Conference on Camera-Based Document Analysis and Recognition; Sep. 22, 2011; 7 pages.

Zeng et al.; "*Audio-Haptic Browser for a Geographical Information System*"; ICCHP 2010, Part II, LNCS 6180; Jul. 14-16, 2010; 8 pages.

(56) References Cited

OTHER PUBLICATIONS

Zhang et al.; "*A Multiple Sensor-Based Shoe-Mounted User Interface Designed for Navigation Systems for the Visually Impaired*"; 5$^{th}$ Annual ICST Wireless Internet Conference (WICON); Mar. 1-3, 2010; 9 pages.

Shidujaman et al.; "Design and navigation Prospective for Wireless Power Transmission Robot;" IEEE; Jun. 2015.

Wu et al. "Fusing Multi-Modal Features for Gesture Recognition", Proceedings of the 15$^{th}$ ACM on International Conference on Multimodal Interaction, Dec. 9, 2013, ACM, pp. 453-459.

Pitsikalis et al. "Multimodal Gesture Recognition via Multiple Hypotheses Rescoring", Journal of Machine Learning Research, Feb. 2015, pp. 255-284.

Shen et al. "Walkie-Markie: Indoor Pathway Mapping Made Easy" 10$^{th}$ USENIX Symposium on Networked Systems Design and Implementation (NSDI'13); pp. 85-98, 2013.

Tu et al. "Crowdsourced Routing II D2.6" 34 pages; 2012.

De Choudhury et al. "Automatic Construction of Travel Itineraries Using Social Breadcrumbs" pp. 35-44; Jun. 2010.

\* cited by examiner

WEARABLE COMPUTING DEVICE HAVING A CURVED BACK TO REDUCE PRESSURE ON VERTEBRAE

BACKGROUND

1. Field

The present disclosure relates to a wearable computing device to be worn around a user's neck that includes a curved back for reducing an amount of pressure applied to vertebra of the user by the device.

2. Description of the Related Art

As computing power becomes faster and electronic devices become smaller, technology is being implemented in increasingly smaller packages. Technology is now at a point in which advanced computing functions can be implemented in devices sufficiently small to be worn by users as accessories. Wearable computing devices, or wearable smart devices, can perform functions for a user without requiring physical manipulation of the device by the user. Examples of wearable computing devices include eyeglasses, watches, and necklaces.

Wearable computing devices perform various functions for users. For example, some wearable computing devices can function as extensions of a mobile phone of the user. Other wearable computing devices perform functions that require a relatively large amount of computation, such as providing social and environmental awareness.

Design of wearable computing devices should take into consideration various factors based on characteristics of the device. In particular, wearable computing devices that can perform computation-heavy social and environmental awareness features may have a greater mass than wearable computing devices that perform less computation-heavy features. If this mass is not well-distributed on a user, it may result in discomfort experienced by the user. Similarly, processors of wearable computing devices that can perform computation-heavy social and environmental awareness features may generate more heat than processors of wearable computing devices that perform less computation-heavy features. If this heat is not well-distributed into the atmosphere, it may result in additional discomfort experienced by the user.

Thus, there is a need for devices and systems for increasing comfort of wearable computing devices that perform computation-heavy social and environmental awareness functions.

SUMMARY

What is described is a wearable computing device designed to be worn around a neck of a user. The wearable computing device includes a first side portion and a second side portion each designed to at least partially extend across a shoulder of the user and to rest on a front of the user. The wearable computing device also includes a neck portion defining a cavity and having a first end connected to the first side portion and a second end connected to the second side portion. The neck portion also includes an outer edge and an inner edge that is positioned nearer the neck of the user than the outer edge when the wearable computing device is worn. The neck portion is curved from the first end to the second end in order to extend around a portion of a circumference of the neck of the user. The neck portion is also curved from the outer edge to the inner edge at a center portion between the first end and the second end in order to follow a curvature of a spine of the user. The wearable computing device also includes an input device designed to detect input data. The wearable computing device also includes a mobile processor positioned in the cavity, coupled to the input device, and designed to determine output data based on the input data. The wearable computing device also includes an output device coupled to the mobile processor and designed to output the output data.

Also described is a wearable computing device designed to be worn around a neck of a user. The wearable computing device includes a first side portion and a second side portion each designed to at least partially extend across a shoulder of the user and to rest on a front of the user. The wearable computing device also includes a neck portion defining a cavity and having a first end connected to the first side portion and a second end connected to the second side portion. The neck portion also includes an outer edge and an inner edge that is positioned nearer the neck of the user than the outer edge when the wearable computing device is worn. The neck portion is curved from the first end to the second end to extend around a portion of a circumference of the neck of the user. The neck portion is also curved from the outer edge to the inner edge at a center portion between the first end and the second end to follow a curvature of a spine of the user. The wearable computing device also includes a camera designed to detect image data. The wearable computing device also includes a mobile processor positioned in the cavity, coupled to the camera, and designed to recognize objects based on the image data and to determine navigation instructions based on the image data. The wearable computing device also includes a speaker coupled to the mobile processor and designed to output data corresponding to the recognized objects or the determined navigation instructions.

Also described is a wearable computing device designed to be worn around a neck of a user. The wearable computing device includes a first side portion and a second side portion each having a rigid portion that rests on a front of the user when the wearable computing device is worn. Each of the first side portion and the second side portion also has a flexible portion that at least partially extends across a shoulder of the user. The wearable computing device also includes a neck portion that defines a cavity and has a first end connected to the flexible portion of the first side portion and a second end connected to the flexible portion of the second side portion. The neck portion also includes a top edge and a bottom edge designed to contact a back of the user at a lower location than the top edge. The neck portion is curved from the top edge to the bottom edge to follow a curvature of a spine of the user. The wearable computing device also includes a camera designed to detect image data. The wearable computing device also includes a mobile processor positioned in the cavity, coupled to the camera, and designed to recognize objects based on the image data and determine navigation instructions based on the image data. The wearable computing device also includes a speaker coupled to the mobile processor and designed to output data corresponding to the recognized objects or the determined navigation instructions.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale, and may be exaggerated to better illustrate the important features of the present invention. In the drawings, like reference numerals designate like parts throughout the different views, wherein:

DETAILED DESCRIPTION

Described herein are wearable computing devices that may be worn around a neck of a user. The wearable computing devices may be relatively heavy and may have a neck portion that rests on a neck or back of the user. The present invention includes a design of the neck portion that provides increased comfort to users. In particular, the neck portion has been designed such that the weight of the wearable computing devices is not applied to any particular vertebra of the user and is relatively evenly distributed about the user's body.

The neck portion has also been designed to increase comfort by reducing an amount of heat experienced by the user. In particular, the neck portion includes various heat distribution devices that receive heat from the electronic components. The heat distribution devices are each connected and are designed in such a way that heat transfers from the electronic components to the heat distribution devices and into the atmosphere.

The wearable computing devices provide several benefits and advantages such as increased comfort to users of the wearable computing device. This allows the user to wear the wearable computing device for longer periods of time. Increased comfort is provided in at least two different ways: by providing an even weight distribution and by distributing heat away from the neck of the user. Distributing heat away from the neck of the user provides additional benefits and advantages such as reducing the likelihood of electronic components overheating, which in turn reduces the likelihood of damage to the electronic components.

Figure 1:
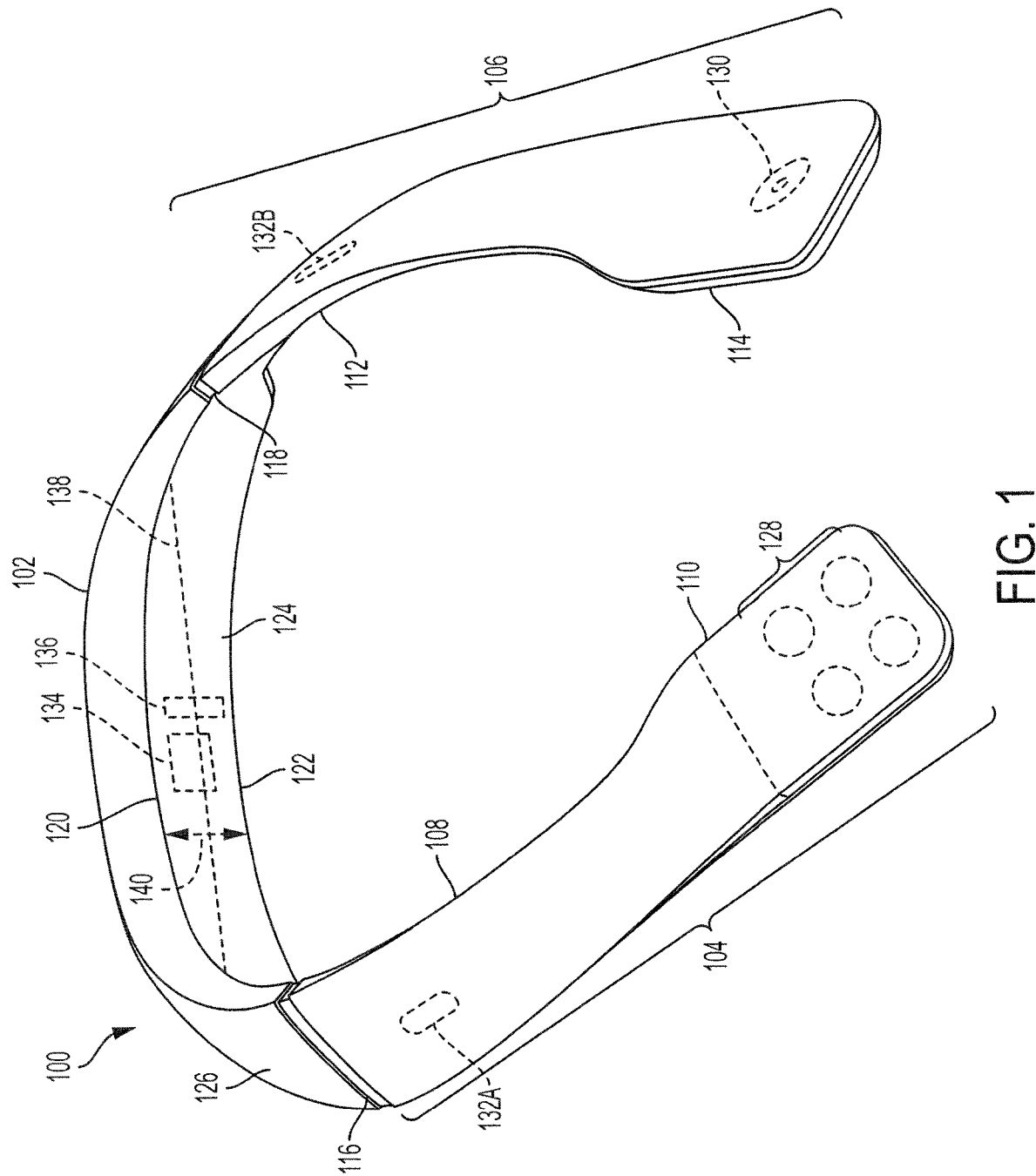
FIG. 1 is a perspective view of a wearable computing device designed to be worn around a neck of a user and that includes two side portions and a neck portion that has features for increasing comfort according to an embodiment of the present invention.

Turning to FIG. 1, a wearable computing device 100 is shown. The wearable computing device 100 is designed to be worn around a neck of a user. In that regard, the wearable computing device 100 includes a neck portion 102 designed to rest on a back of a neck of the user and to extend around at least a portion of a circumference of the neck of the user. The wearable computing device 100 also includes a first side portion 104 and a second side portion 106. The side portions 104, 106 are designed to extend across a user's shoulder and to rest on a front of a user, such as on a chest of the user.

The first side portion 104 includes a first flexible portion 108 and a first rigid portion 110. The second side portion 106 includes a second flexible portion 112 and a second rigid portion 114. The first flexible portion 108 is positioned between the neck portion 102 and the first rigid portion 110. The first flexible portion 108 may be coupled to a first end 116 of the neck portion 102, and the second flexible portion 112 may be coupled to a second end 118 of the neck portion 102. In that regard, the first flexible portion 108 may extend across the shoulder of the user and may be malleable or flexible such that it may follow the contours of the shoulder of the user. The first rigid portion 110 may rest on a portion of the front of the user, such as on the chest of the user.

Figure 3:
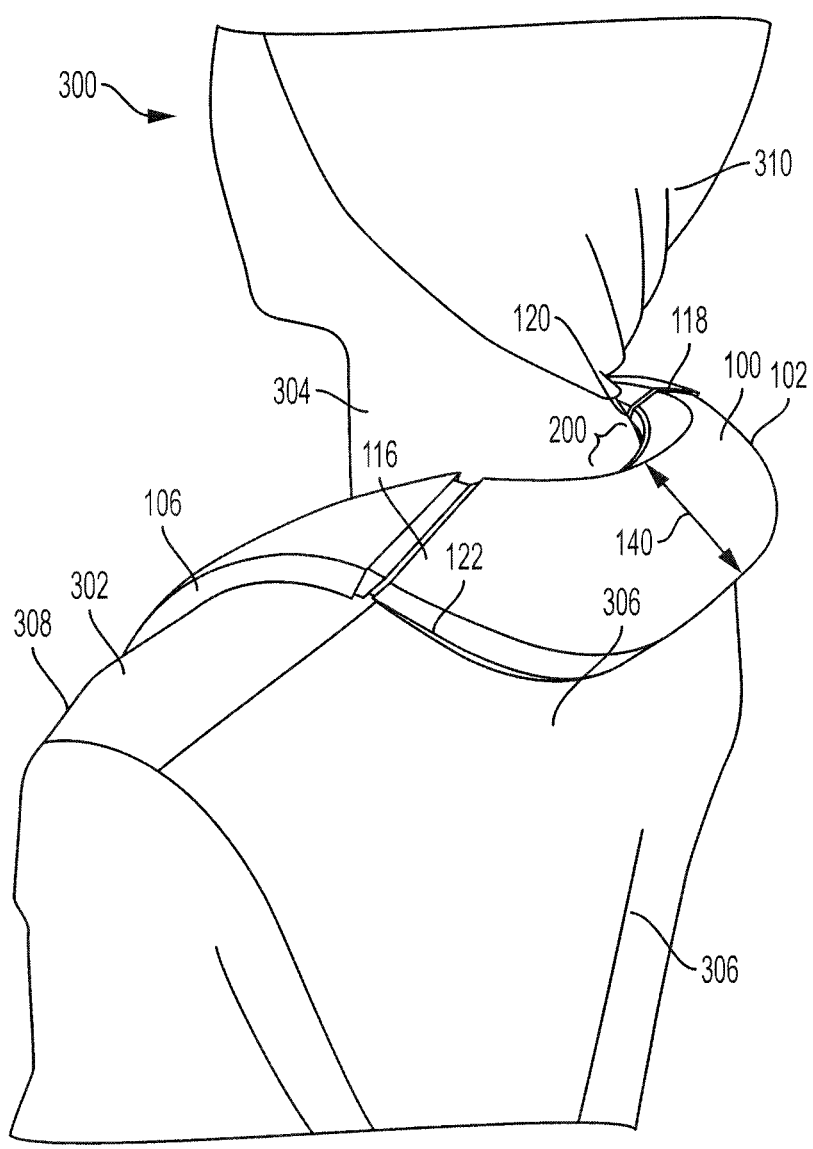
FIG. 3 illustrates a view of the wearable computing device of FIG. 1 as worn by a user according to an embodiment of the present invention.

The neck portion 102 may include a top edge or inner edge 120 and a bottom edge or outer edge 122. The inner edge 120 may correspond to an edge that is nearer a center of the wearable computing device 100 than the outer edge 122. When the wearable computing device 100 is worn by a user, as shown in FIG. 3, the inner edge 120 may be nearer to a head of the user than the outer edge 122.

The neck portion 102 may also include a contact surface 124 and an exposed surface 126. The exposed surface 126 may be on an opposite side of the neck portion 102 from the contact surface 124. When the wearable computing device 100 is worn by a user, as shown in FIG. 3, the contact surface 124 may be in contact with a neck or a back of the user and the exposed surface 126 may be exposed to the environment. The contact surface 124 and/or the exposed surface 126 may refer to the neck portion 102 and/or to the entire wearable computing device 100.

The wearable computing device 100 may include multiple features for providing situational awareness to a user. For example, the wearable computing device 100 may provide assistance to a blind user by providing information to the blind user regarding objects in the environment, providing navigation instructions to the blind user, or the like.

The wearable computing device 100 may include one or more input devices for receiving input. The input devices may be used to receive user input, may detect data corresponding to the environment of the user, may receive a communication signal, or the like. For example, the wearable computing device 100 may include one or more buttons 128 for receiving user input. In some embodiments, a user may select a mode of operation of the wearable computing device 100 via the one or more buttons 128.

The wearable computing device 100 may also include one or more camera 130, such as a single camera, a stereo pair of cameras, a wide angle camera, or the like. The camera 130 may detect image data corresponding to the environment of the user.

The wearable computing device 100 may also include one or more output devices for providing output data to the user. The output devices may provide audio feedback, haptic feedback, visual feedback, or the like to the user. For example, the wearable computing device 100 may include a first output unit 132A and a second output unit 132B. The first output unit 132A and the second output unit 132B may each provide audio and haptic output. In that regard, the first output unit 132A and the second output unit 132B may together provide stereo feedback to the user. For example, the first output unit 132A and the second output unit 132B may each output audio data providing an identification of an object in the environment. As another example, the first output unit 132A and the second output unit 132B may provide navigation instructions via audio feedback and/or via stereo haptic feedback.

The wearable computing device 100 may include a mobile processor 134 and a memory 136. In some embodiments, the neck portion 102 defines a cavity in which the mobile processor 134 and/or the memory 136 are positioned. The memory 136 may include any memory for storing non-transitory data including instructions to be performed by the mobile processor 134. The mobile processor 134 may receive input data from the buttons 128 and/or the camera 130. The mobile processor 134 may then determine output data based on the input data and cause the first output unit 132A and the second output unit 132B to output the output data.

The wearable computing device 100 may operate in four modes: explorer mode, scan mode, find mode and capture mode. Each of the buttons 128 may correspond to one mode. For example, one button may correspond to the explorer mode and another button may correspond to the scan mode.

While in the explorer mode, the wearable computing device 100 provides data to the user associated with the surroundings of the user. In some embodiments, the wearable computing device 100 may describe data detected by the camera 130. The data may include predefined data, such as hazard data, whether a friend of the user is passing by, whether a user's favorite restaurant is detected, etc.

While in the scan mode, the wearable computing device 100 may describe everything that is in the field of view of the camera 130. For example, the wearable computing device 100 may describe everything in the field of view, such as by telling the user that object X is 50 degrees to your left, object Y is at your eleven-o'clock, objects Z and W are directly ahead, or the like.

While in the find mode, the wearable computing device 100 can navigate the user to a desired object, place, person, or the like. The user can provide data about the desired object, place, person, or the like, such as by speaking the name or address of the object, place, person, or the like. The wearable computing device 100 can then determine the location of the object, place, person, or the like and provide navigation directions to the user.

The capture mode may allow the wearable computing device 100 to store its current location in the memory 16 so that it can guide the user back to the same location at a later time. The capture mode may include 2 instructions—capture and return. Capture stores the location information (and possibly any obstacles that may arise during a return trip to the position) while return causes the wearable computing device 100 to provide navigation instructions to the user for a return to the location. In various embodiments, a single press of the capture button may indicate the capture instruction and a double click indicates the return instruction.

The wearable computing device 100 may be worn for a relatively long period of time. In that regard, it is desirable for the wearable computing device 100 to be comfortable when worn by a user. It is been shown that comfort of a necklace is increased when pressure on one or more vertebra is decreased. Thus, the neck portion 102 of the wearable computing device 100 includes features for more evenly distributing the weight of the wearable computing device 100 on the user and for decreasing pressure applied to any one or more vertebra by the wearable computing device 100.

One such feature is that the neck portion 102 curves from the first end 116 to the second end 118 to extend around at least a portion of a neck of the user. The neck portion 102 includes a longitudinal axis 138 that may be substantially perpendicular to a longitudinal axis of the first side portion 104 and the second side portion 106. The neck portion 102 may be curved from the longitudinal axis in order to connect with the first side portion 104 and the second side portion 106 while maintaining curvature allowing it to extend around the neck.

The neck portion 102 also includes a width 140 extending from the inner edge 120 to the outer edge 122. Thus, the contact surface 124 may be in contact with the user along the width 140 of the neck portion 102. At least a portion of the contact surface 124 may be bowed outward (i.e., bowed towards the exposed surface 126), such that a concave cavity is defined by the contact surface 124. This bowing of the contact surface 124 results in a curvature that follows a curvature of a spine of the user. For example, the curvature of the contact surface 124 may resemble the curvature from a cervical portion of the spine to a thoracic portion of the spine.

Figure 2A:
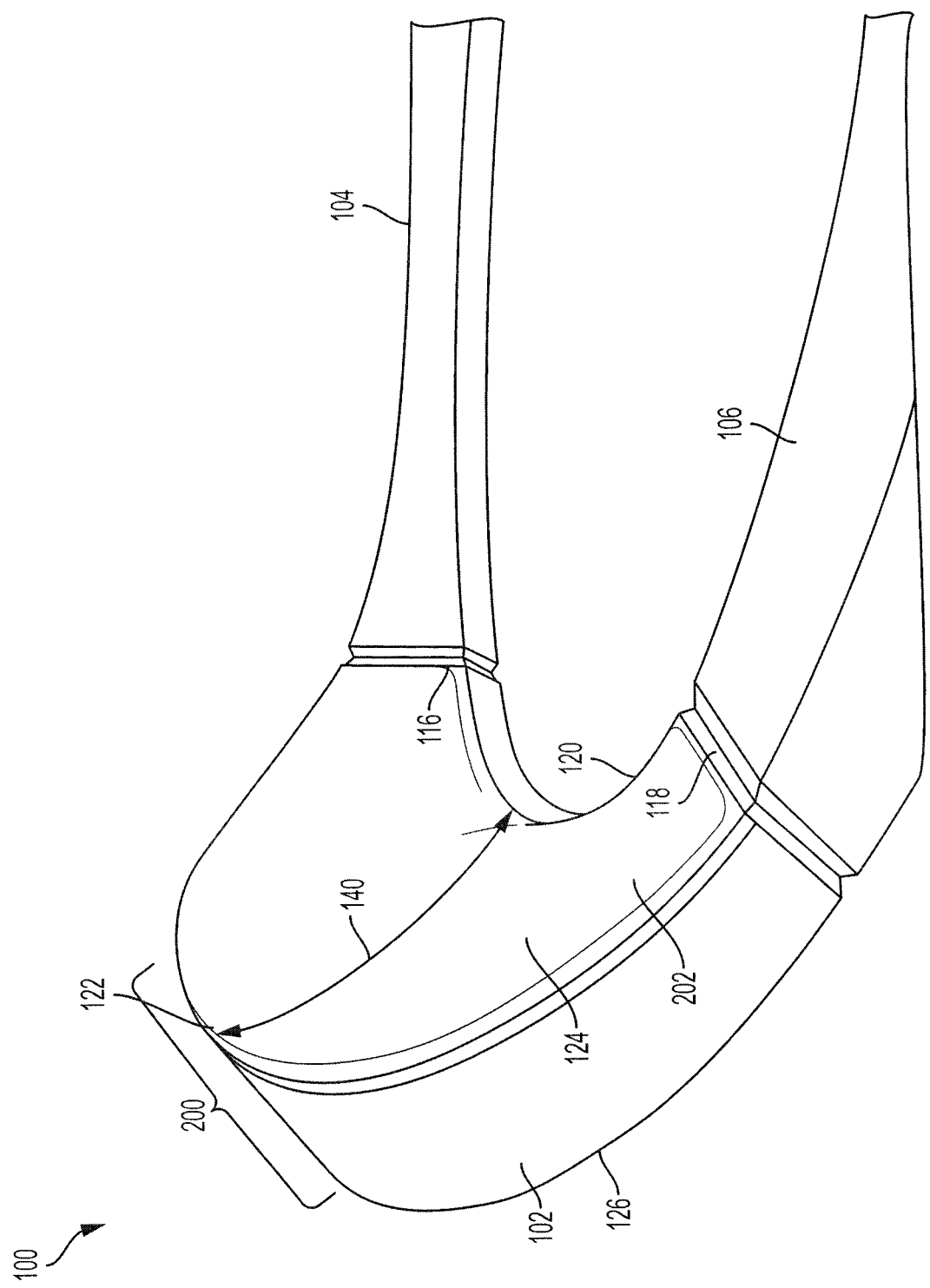
FIG. 2A illustrates an enlarged view of the neck portion of FIG. 1 showing a curvature from an inner edge of the neck portion to an outer edge of the neck portion that is designed to follow a curvature of a spine according to an embodiment of the present invention.

Turning to FIG. 2A, a close-up view of the neck portion 102 illustrates the curvature of the neck portion 102. In particular, FIG. 2A illustrates the curvature of the neck portion 102 from the first end 116 to the second end 118. This curvature may result in the neck portion 102 having a substantially "U" shape from the first side portion 104 to the second side portion 106.

The neck portion 102 may have a center portion 200 positioned between the first end 116 and the second end 118 and extending along the width 140. As shown, the curvature of the neck portion 102 from the inner edge 120 to the outer edge 122 may occur along the width 140 at the center portion 200 of the neck portion 102. In that regard, when the wearable computing device 100 is worn, the contact surface 124 along the center portion 200 may rest flush with the user's spine. This curvature reduces an amount of force applied by the neck portion 102 to any one or more vertebra of the user, thus increasing comfort of the wearable computing device 100.

The neck portion 102 may also include a padding 202 that defines the contact surface 124. The padding 202 may be coupled to a casing of the neck portion 102 and may further distribute the weight of the wearable computing device 100. The padding 202 may include material such as silicon, foam, rubber, or any other material capable of providing cushioning or padding.

Figure 2B:
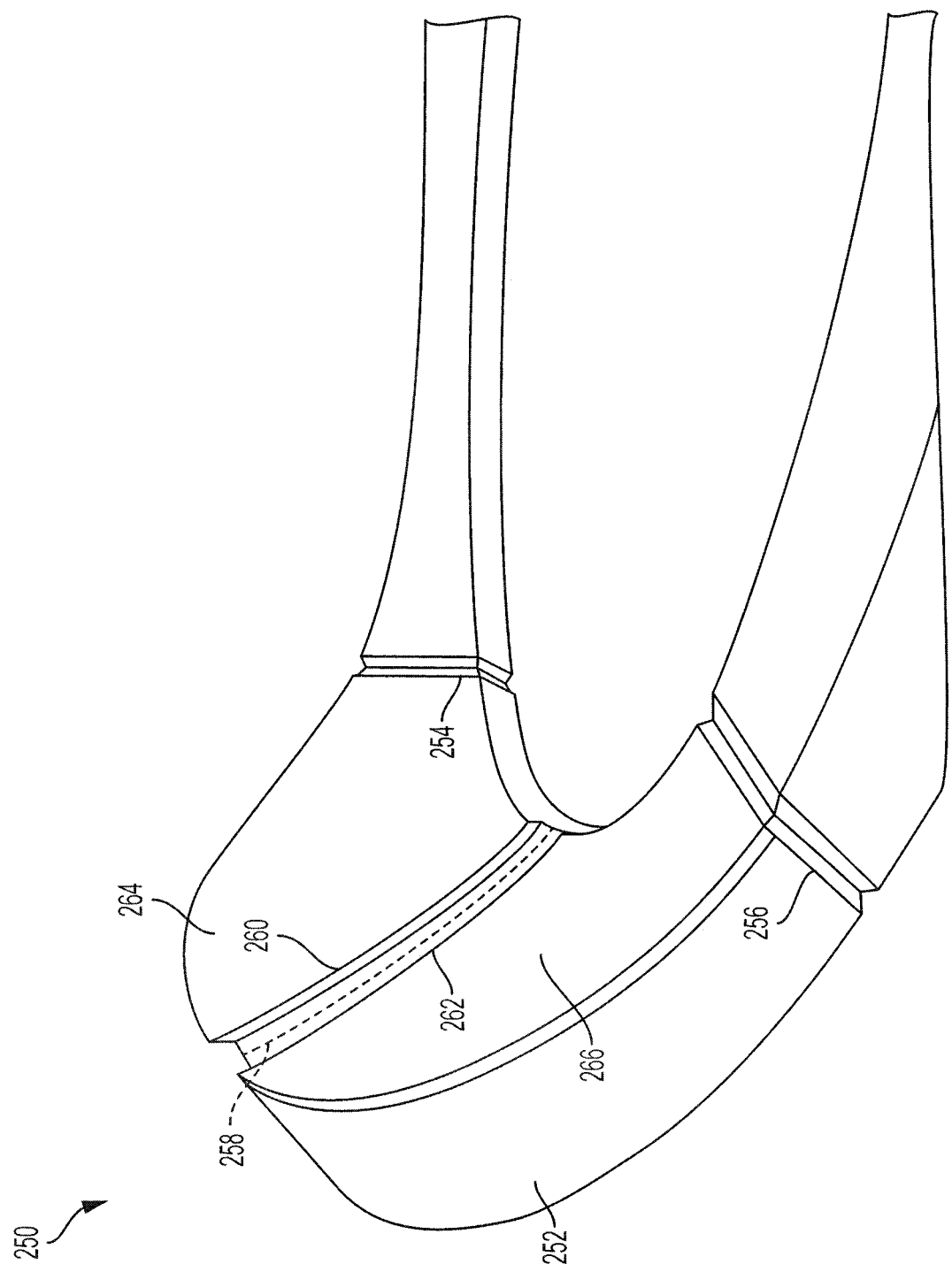
FIG. 2B illustrates an enlarged view of a neck portion of a wearable computing device that has padding on a contact surface of both sides of the neck portion and does not include padding at a center location such that a spine is positioned between the padding to reduce pressure on the spine according to an embodiment of the present invention.

Turning to FIG. 2B, a neck portion 252 of another wearable computing device 250 may include different features than the neck portion 102 of FIG. 2A. The neck portion 252 has a first end 254, a second end 256, and a curvature between the first end 254 and the second end 256. The neck portion 252 may also have a curvature from an inner edge to an outer edge. The neck portion 252 may include padding having different features than the padding 202 of FIG. 2B. For example, the neck portion 252 may include a first padding 264 and a second padding 266.

The first padding 264 may span from the first end 254 to a first location 260 positioned away from a halfway point 258 of the neck portion 252. The second padding 266 may span from the second end 256 to a second location 262 positioned away from the halfway point 258 of the neck portion 252.

No padding may exist between the first location 260 and the second location 262. When the wearable computing device 250 is worn, the first padding 264 and the second padding 266 may contact the user's neck, back, and/or shoulders. However, because no padding exists between the first location 260 and the second location 262, the neck portion 252 may not contact the spine of the user or may make minimal contact with the spine of the user. Thus, use of the first padding 264 and the second padding 266 may reduce pressure applied to the user's spine by the neck portion 252 even more so than the design of the neck portion 102 of FIG. 2A.

Turning now to FIG. 3, the wearable computing device 100 is shown as worn by a user 300. As shown, the neck portion 102 at least partially rests on a neck 304 and/or a back 306 of the user 300. The inner edge 120 of the neck portion 102 is positioned higher on the back 306 of the user 300 than the outer edge 122. Thus, the inner edge 120 is positioned nearer to a head 310 of the user 300 than the outer edge 122. In some embodiments, the inner edge 120 may be substantially parallel to the shoulder 302 of the user 300. Stated differently, the inner edge 120 may be positioned at substantially the same height as the user's shoulder 302.

FIG. 3 illustrates how the curvature of the neck portion 102 from the first end 116 to the second end 118 resembles a curvature of the neck 304 of the user 300. This allows the neck portion 102 to extend from a first side of the neck 304 to a second side of the neck 304. From the first end 116, the first side portion 104 extends from the first end 116 of the neck portion 102 over the shoulder 302 and rests on a front 308 of the user 300.

Figure 4:
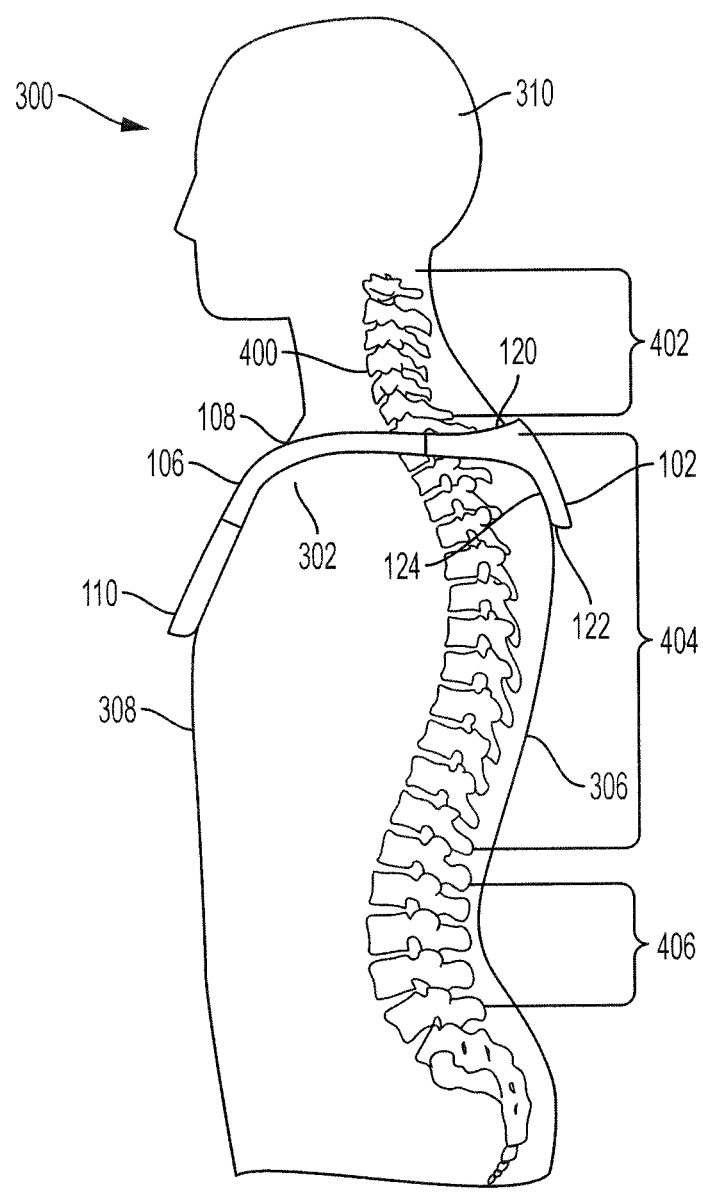
FIG. 4 illustrates another view of the wearable computing device of FIG. 1 as worn by a user and shows a spine of the user to illustrate how the curvature illustrated in FIG. 2B follows a curvature of the spine according to an embodiment of the present invention.

Referring now to FIG. 4, a cross-sectional view of the wearable computing device 100 as worn on the user 300 is shown. A spine 400 of the user is shown to illustrate how the curvature of the neck portion 102 resembles the curvature of the spine 400. The spine 400 includes a cervical portion 402, a thoracic portion 404, and a lumbar portion 406. The spine 400 has a curvature between the cervical portion 402 and the thoracic portion 404. As shown, the contact surface 124 of the neck portion 102 has a curvature that resembles the curvature of the spine 400 between the cervical portion 402 and the thoracic portion 404. Thus, the curvature of the contact surface 124 reduces an amount of pressure applied to any vertebrae of the spine 400 by the wearable computing device 100 by more evenly distributing contact with the user 300.

As shown, the first flexible portion 108 extends across the shoulder 302 towards the front 308 of the user 300. In some embodiments, the first flexible portion 108 may extend along a portion of the front 308 of the user 300. The first rigid portion 110 may rest on the front 308 of the user 300. In that regard, it may be desirable for the first rigid portion 110 to have a relatively flat contact surface such that it may rest on a flat portion of the front 308 of the user 300.

Figure 5:
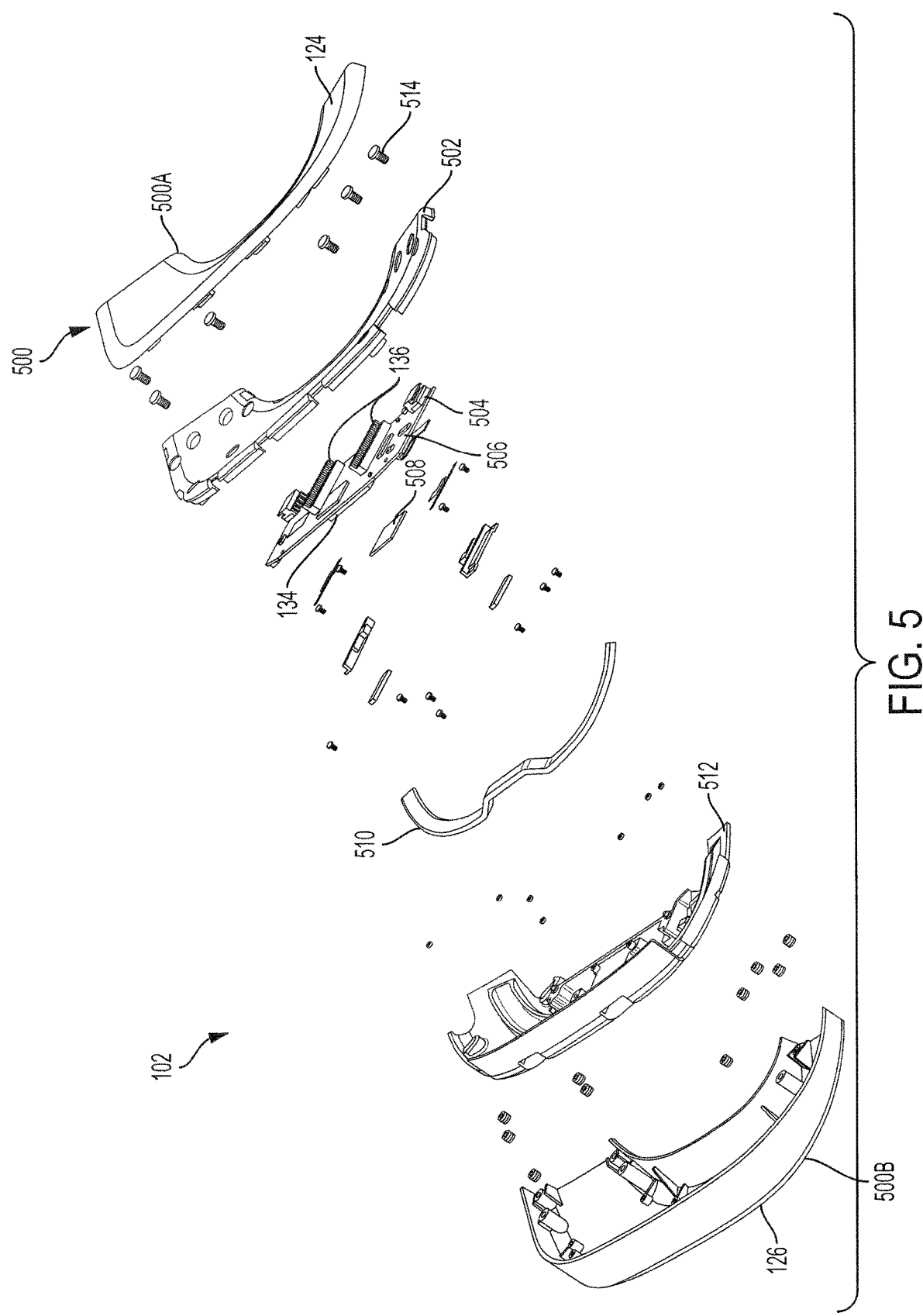
FIG. 5 is an exploded view of the wearable computing device of FIG. 1 illustrating various features for distributing heat away from a mobile processor according to an embodiment of the present invention.

Turning now to FIG. 5, an exploded view of the neck portion 102 illustrates various features of the neck portion 102 for dissipating heat. The neck portion 102 includes a housing 500 having an inner housing 500A and an outer housing 500B. The housing 500 may include metal, plastic, or another rigid material that provides a structure for the components of the neck portion 102. Stated differently, the housing 500 may define a cavity in which components of the neck portion 102 are positioned.

The inner housing 500A may define the contact surface 124 and the outer housing 500B may define the exposed surface 126. In some embodiments, additional padding may be coupled to the contact surface 124 of the inner housing 500A, thus creating a new contact surface that includes the padding.

A printed circuit board (PCB) mount 502 may be positioned within the housing 500. In some embodiments, the PCB mount 502 may be coupled to the inner housing 500A. The PCB mount 502 may include metal, plastic, or another rigid material on which a PCB may be mounted.

A motherboard 504 may include the mobile processor 134 and the memory 136 positioned on and electrically coupled via a PCB 506. The motherboard 504 may be mounted on the PCB mount 502. For example, the motherboard 504 may be coupled to the PCB mount 502 via a snap-fit connection, a press-fit connection, fasteners, or the like.

Because the mobile processor 134 may perform computation-heavy social and environmental awareness functions, it may generate a relatively large amount of heat during operation. It is desirable to dissipate this heat away from the neck portion 102 in order to increase comfort of the user. Thus, the neck portion 102 may include various features for dissipating the heat generated by the mobile processor 134.

The neck portion 102 may include a thermal pad 508 that is coupled to the mobile processor 134. The thermal pad 508 may include a material having a relatively low resistance that is capable of transferring heat. The thermal pad 508 may partially or fully contact a surface of the mobile processor 134.

A pipe 510 may be coupled to the thermal pad 508 and may receive heat from the mobile processor 134 via the thermal pad 508. The pipe 510 may include a metal, such as copper. In that regard, the pipe 510 may have a relatively low resistance and be capable of transferring heat.

A heat spreader 512 may be coupled to the pipe 510 via thermal paste (not shown). The thermal paste may include any spreadable material capable of conducting heat. The heat spreader 512 may include any material capable of conducting heat. For example, the heat spreader 512 may include a metal such as aluminum, copper, or the like. The heat spreader 512 may receive heat from the mobile processor 134 via the thermal pad 508, the pipe 510, and the thermal paste.

The heat spreader 512 may have a relatively large surface area. In that regard, heat received by the heat spreader 512 may be dissipated, or spread, into the atmosphere and/or to the outer housing 500B from various surfaces of the heat spreader 512. Because the heat spreader 512 has a relatively large surface area, heat may be distributed over a relatively large area. This reduces the likelihood of any single location of the neck portion 102 having a relatively high temperature.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A wearable computing device, comprising:
a first side portion and a second side portion each configured to at least partially extend across a shoulder of a user and to rest on a front of the user;
a neck portion having an inner housing and an outer housing configured to be coupled together and to define a cavity, the neck portion having a first end connected to the first side portion, a second end connected to the second side portion, a center portion that is in between the first end and the second end and that has a width that extends from a neck of the user to a thoracic portion of a spine of the user, an outer edge, an inner edge that is positioned nearer the neck of the user than the outer edge when the wearable computing device is worn, a contact surface that extends the width of the center portion and is configured to contact and rest flush with the thoracic portion of the spine of the user when the wearable computing device is worn, and an exposed surface defined by the outer housing and oriented opposite the contact surface, a curvature of the neck portion extending from the inner edge to the outer edge along the width of the center portion;
an input device configured to detect input data;
a mobile processor positioned in the cavity, coupled to the input device, and configured to determine output data based on the input data;
an output device coupled to the mobile processor and configured to output the output data;
a thermal pad positioned in the cavity, in contact with the mobile processor such that the mobile processor is located between the thermal pad and the contact surface, and configured to transfer heat from the mobile processor; and
a heat spreader located in the cavity and configured to distribute the heat from the mobile processor via the thermal pad.

2. The wearable computing device of claim 1 further comprising a padding coupled to the neck portion and configured to contact the user when the wearable computing device is worn.

3. The wearable computing device of claim 2 wherein the padding includes a first padding that extends from a first location away from a halfway point along the width of the neck portion to the first end of the neck portion and a second padding that extends from a second location away from the halfway point to the second end of the neck portion such that the spine of the user is positioned between the first padding and the second padding when the wearable computing device is worn.

4. The wearable computing device of claim 1 wherein the inner edge of the neck portion is positioned at a height that is substantially equal to a height of shoulders of the user when the wearable computing device is worn.

5. The wearable computing device of claim 1 wherein the mobile processor is further configured to operate in a first mode in which it generates navigation instructions to a desired location and in a second mode in which it recognizes objects in an environment.

6. The wearable computing device of claim 1 wherein the output device includes a first output unit and a second output unit that each include a speaker and a vibration unit for providing at least one of stereo audio output or stereo haptic output.

7. The wearable computing device of claim 1 wherein the curvature from the inner edge of the neck portion to the outer edge of the neck portion resembles a curvature of the spine of the user from a cervical portion of the spine to the thoracic portion of the spine.

8. The wearable computing device of claim 1 wherein each of the first side portion and the second side portion includes a rigid portion configured to rest on the front of the user when the wearable computing device is worn, and a flexible portion positioned between the rigid portion and the neck portion and configured to at least partially extend across the shoulder of the user.

9. A wearable computing device, comprising:
a first side portion and a second side portion each configured to at least partially extend across a shoulder of a user and to rest on a front of the user;
a neck portion having an inner housing and an outer housing configured to be coupled together and to define a cavity, the neck portion having a first end connected to the first side portion, a second end connected to the second side portion, a center portion that in between the first end and the second end and that has a width that extends from a neck of the user to a thoracic portion of a spine of the user, an outer edge, an inner edge that is positioned nearer the neck of the user than the outer edge when the wearable computing device is worn, a contact surface that extends the width of the center portion and is configured to contact and rest flush with the thoracic portion of the spine of the user when the wearable computing device is worn, and an exposed surface defined by the outer housing and oriented opposite the contact surface, a curvature of the neck portion extending from the inner edge to the outer edge along the width of the center portion;
a padding that is coupled to the neck portion and spans the entire contact surface to distribute weight on the user;
a camera configured to detect image data;
a mobile processor positioned in the cavity, coupled to the camera, and configured to recognize objects based on the image data and determine navigation instructions based on the image data;
a speaker coupled to the mobile processor and configured to output data corresponding to the recognized objects or the determined navigation instructions;
a thermal pad positioned in the cavity, in contact with the mobile processor such that the mobile processor is located between the thermal pad and the contact surface, and configured to transfer heat from the mobile processor; and
a heat spreader located in the cavity and configured to distribute the heat from the mobile processor via the thermal pad.

10. The wearable computing device of claim 9 wherein the inner edge of the neck portion is positioned at a height that is substantially equal to a height of shoulders of the user when the wearable computing device is worn.

11. The wearable computing device of claim 9 wherein the speaker includes a first output unit and a second output unit that each include a combined speaker and vibration unit for providing at least one of stereo audio output or stereo haptic output.

12. The wearable computing device of claim 9 wherein the curvature from the inner edge of the neck portion to the outer edge of the neck portion resembles a curvature of the spine of the user from a cervical portion of the spine to the thoracic portion of the spine.

13. The wearable computing device of claim 9 wherein each of the first side portion and the second side portion includes a rigid portion configured to rest on the front of the user when the wearable computing device is worn, and a flexible portion positioned between the rigid portion and the neck portion and configured to at least partially extend across the shoulder of the user.

14. A wearable computing device designed to be worn around a neck of a user comprising:
    a first side portion and a second side portion each having a rigid portion configured to rest on a front of the user when the wearable computing device is worn, and a flexible portion configured to at least partially extend across a shoulder of the user;
    a neck portion having an inner housing and an outer housing configured to be coupled together and to define a cavity, the neck portion having a first end connected to the flexible portion of the first side portion, a second end connected to the flexible portion of the second side portion, a top edge, a bottom edge configured to contact a back of the user at a lower location than the top edge, a contact surface defined by the inner housing and configured to contact the user, and an exposed surface defined by the outer housing and oriented opposite the contact surface, the contact surface being bowed towards the exposed surface along a width of the neck portion between the top edge and the bottom edge to resemble a curvature of a spine of the user;
    a padding that is coupled to the neck portion and spans the entire contact surface to distribute weight on the user;
    a camera configured to detect image data;
    a mobile processor positioned in the cavity, coupled to the camera, and configured to recognize objects based on the image data and determine navigation instructions based on the image data;
    a speaker coupled to the mobile processor and configured to output data corresponding to the recognized objects or the determined navigation instructions;
    a thermal pad positioned in the cavity, in contact with the mobile processor such that the mobile processor is located between the thermal pad and the contact surface, and configured to transfer heat from the mobile processor; and
    a heat spreader located in the cavity and configured to distribute the heat from the mobile processor via the thermal pad.

15. The wearable computing device of claim 14 wherein the top edge of the neck portion is positioned at a height that is substantially equal to a height of shoulders of the user when the wearable computing device is worn.

16. The wearable computing device of claim 14 wherein a curve from the top edge of the neck portion to the bottom edge of the neck portion resembles the curvature of the spine of the user from a cervical portion of the spine to a thoracic portion of the spine.

* * * * *